(12) United States Patent
Stempfle et al.

(10) Patent No.: US 7,905,860 B2
(45) Date of Patent: Mar. 15, 2011

(54) PLUNGER DISC LOADING MECHANISM FOR SYRINGE PUMP

(75) Inventors: Julius Stempfle, Suwanee, GA (US); Chang-Jung Lee, Alpharetta, GA (US)

(73) Assignee: Elixir Corp., Suwanee, GA (US)

( * ) Notice: Subject to any disclaimer, the term of this patent is extended or adjusted under 35 U.S.C. 154(b) by 49 days.

(21) Appl. No.: 12/204,889

(22) Filed: Sep. 5, 2008

(65) Prior Publication Data

US 2010/0063447 A1   Mar. 11, 2010

(51) Int. Cl.
    *A61M 1/00* (2006.01)
(52) U.S. Cl. ............................................. 604/151
(58) Field of Classification Search ............ 604/131, 604/151–155
    See application file for complete search history.

(56) References Cited

U.S. PATENT DOCUMENTS

| | | | |
|---|---|---|---|
| 4,424,720 A * | 1/1984 | Bucchianeri | 74/424.78 |
| 5,814,015 A * | 9/1998 | Gargano et al. | 604/67 |
| 6,428,509 B1 * | 8/2002 | Fielder | 604/154 |
| 6,551,277 B1 * | 4/2003 | Ford | 604/131 |
| 6,575,936 B1 * | 6/2003 | Kojima et al. | 604/155 |
| 7,153,290 B2 | 12/2006 | Wakabayashi | |
| 2004/0073161 A1 * | 4/2004 | Tachibana | 604/67 |

* cited by examiner

*Primary Examiner* — Theodore J Stigell
(74) *Attorney, Agent, or Firm* — Wang Law Firm; Li K. Wang

(57) ABSTRACT

A syringe pump is equipped with mechanism for easy handling of syringes of different sizes. The syringe pump is equipped with a plunger holding device. The plunger holding device includes a retainer housing with two retainer bars. The plunger holding device also includes two handles and a sensing plate. When two handles move toward each other, the retainer housing moves forward and two retainer bars moves away from each other. When two handles are released, the retainer housing slides back over a dowel pin attached to the sensing plate and the retainer bars return to their initial position. A plunger's disc can be securely held by the retainer bars without introducing error in the sensing of the pushing force of the syringe plunger.

12 Claims, 10 Drawing Sheets

PLUNGER DISC LOADING MECHANISM FOR SYRINGE PUMP

FIELD OF THE INVENTION

The invention relates to infusion pump, and more particularly, to a syringe plunger disc loading mechanism for syringe pump.

BACKGROUND OF THE INVENTION

Continuous delivery of medicinal fluid to a patient has been proven beneficial in instances of severe pain, infection, and other medical ailments. Medicinal fluid is often parenterally infused to treat humans and/or animals. The medicinal liquid is infused in a predetermined flow pattern (continuous, intermittent, or variable), and, in some cases, the infusion therapy can last a long time. For example, there are cases which require infusion of drugs, antibiotics, lipids, blood, blood products, enteral solutions, or other therapeutic solutions.

One common apparatus for infusing fluid into a patient is a syringe pump. A syringe pump is a device on which a syringe (usually disposable) with fluid is loaded and the pump drives the syringe plunger to deliver the fluid inside the syringe. The syringe barrel is secured on the pump and the syringe plunger disc is pushed by the pump's plunger driver. The plunger driver is driven by a leadscrew mechanism that is attached to a gearbox/motor assembly located inside the pump. A clutch lever is used to operate a clutch mechanism to engage or disengage the plunger driver from the leadscrew. Thus, the plunger driver can be positioned at the end of the syringe plunger disc to be ready for driving the syringe plunger. The syringe plunger disc has to be secured by the plunger driver to prevent the possibility of over-infusion due to uncontrolled siphoning.

Almost all syringe pumps have a guard gate integrated with the plunger driver to protect the plunger from siphoning. Normally, the loading of the syringe plunger disc is performed after the syringe barrel is firmly loaded onto the syringe pump. If the guard gate is a fixed structure, the user must use one hand to lift the syringe plunger disc over the guard gate and the other hand to actuate the clutch lever to position the plunger driver. Generally, the plunger disc is protected only on the lower side, this fixed type is not only inconvenient but also does not work well for different syringe sizes. The plunger disc can inadvertently become disengaged during use, which can result in over-delivery of the medical fluid and cause harm to a patient. The newer syringe pumps have moving or swinging gates that can be moved or swung out when the clutch lever is actuated to position the plunger driver. The gates will move or swing back to be in front of the plunger disc when the clutch lever is released. Since the thickness of the plunger disc varies for difference syringe sizes, there will be a gap between the gates and the plunger disc if the moving gates cannot move toward the plunger disc to apply force onto the plunger disc to firmly hold the plunger disc onto the plunger driver. Fluctuation of the pressure in the infusion line can affect the plunger disc position and the infusion accuracy if there is a gap between the guard gate and the plunger disc. Due to this gap, the plunger disc is more likely to become disengaged from the guard gate and can cause harm to the patient.

Therefore, there is a need for a syringe pump that provides an easy syringe loading operation and secures firmly the syringe plunger disc during the operation, and it is to this apparatus the present invention is primarily directed to.

SUMMARY OF THE INVENTION

The present invention provides an improved syringe pump with ease and secured loading of the syringe plunger disc. The syringe pump comprises a housing, a syringe saddle attached to the housing, a syringe barrel clamp attached to the housing, a sliding track connected to the housing, a plunger holding device attached to the sliding track, a first movable retainer bar and a second movable retainer bar connected to the plunger holding device, and an activation mechanism connected to the plunger holding device for moving the first movable retainer bar and the second movable retainer bar away from the plunger holding device and away from each other. A disc of a plunger can be held by the first movable retainer bar and the second movable retainer bar and between two movable retainer bars and the plunger holding device.

In another embodiment, there is provided a method for loading and securing a syringe on a syringe pump. The method includes the steps of placing the barrel of a syringe on a syringe saddle of the syringe pump, moving forward a retainer housing, separating two movable retainer bars connected to the retainer housing away from each other, placing the plunger disc between two movable retainer bars, sliding the retainer housing back over a dowel pin of the syringe pump, and securing a disc of the plunger between the two movable retainer bars.

In yet another embodiment, there is provided a syringe pump. The syringe pump comprises means for housing a control circuitry, means for holding a syringe, means for locking the syringe in a position, means for holding a plunger means for moving the means for holding a plunger along an axis, a first retainer means and a second retainer means for holding a disc of the plunger, and means for moving the first retainer means away from the second retainer means. The means for holding the syringe is attached to the means for housing a control circuitry, and the means for locking the syringe is attached to the means for housing a control circuitry. The first retainer means and the second retainer means are connected to the means for holding the plunger.

BRIEF DESCRIPTION OF THE DRAWINGS

Features and advantages of embodiments of the invention will become apparent as the following Detailed Description proceeds, and upon reference to the Drawings, where like numerals depict like elements, and in which.

DETAILED DESCRIPTION OF THE INVENTION

Figure 1:
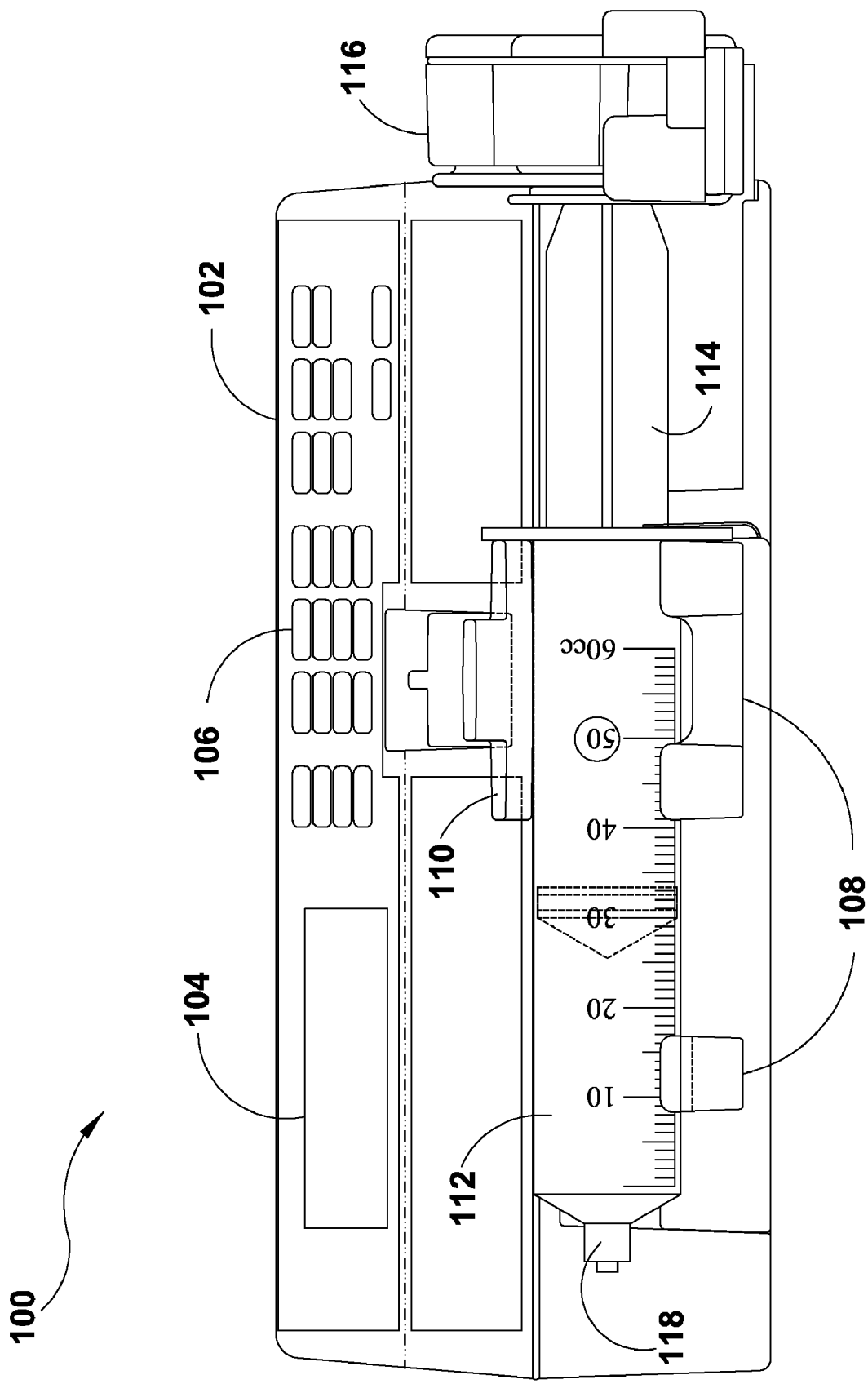
FIG. 1 illustrates a front view of a syringe pump with a syringe loaded according to one embodiment of the invention.

The present invention provides a syringe pump with a plunger disc holding device that enables easy loading of syringes and securely holding the syringe plunger discs of different diameters. FIG. 1 illustrates generally a syringe pump 100 according to the invention. The syringe pump 100 has a housing 102, a control panel 106, a display unit 104, a syringe saddle 108, a syringe barrel clamp 110, and a plunger holding device 116. The housing 102 is for housing control circuitry. The syringe 112 is placed on the top of the syringe saddle 108 and secured by the syringe barrel clamp 110. The syringe barrel clamp 110 is equipped with a spring or a spring-like device that allows the syringe barrel clamp 110 to be lifted and to exert some pressure on the syringe barrel for securing the syringe barrel in place. Skill in the art will appreciate that other holding and locking means used by prior art devices may also be used to hold and lock the syringe in position. The syringe's plunger is placed at and secured by the plunger holding device 116. The plunger holding device 116 is attached to a slidable track 408 (shown in FIG. 4). There is a leadscrew inside of the slidable track 408 that enables the slidable track 408 and the plunger holding device 116 to move along the axis of the leadscrew. Those skilled in the art will appreciate that other moving means may also be used to move the plunger holding device 116. As the slidable track 408 moves toward the housing 102, the syringe plunger 114 moves inside the syringe 112 and forces fluid inside the syringe 112 out from the nozzle 118. The speed with which the fluid is delivered can be controlled easily through the control panel 106 and the syringe plunger 114 can be easily engaged to the plunger holding device 116 without lifting the syringe plunger 114 after the syringe 112 is secured by the syringe saddle 108 and syringe barrel clamp 110.

Figure 2:
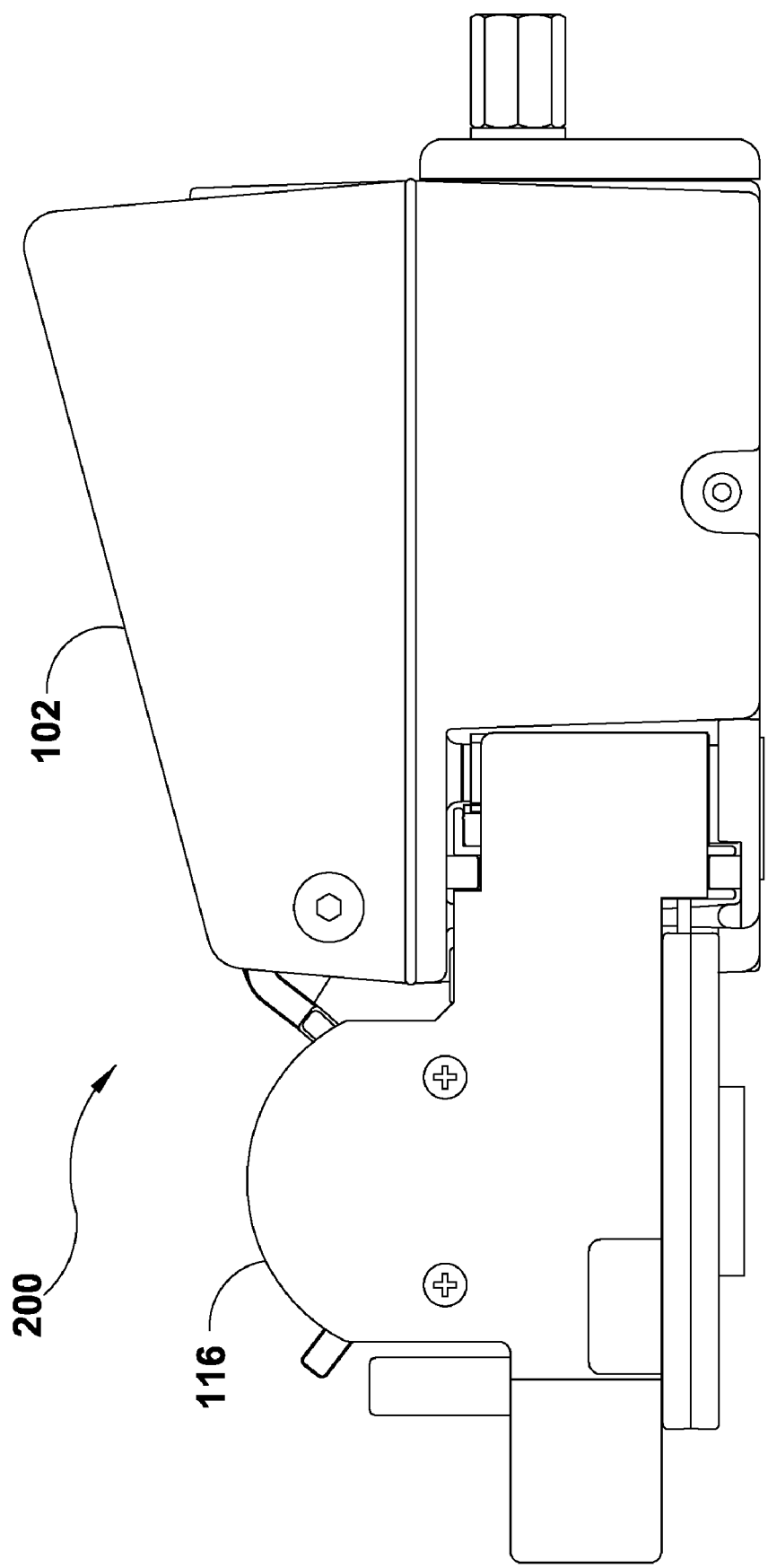
FIG. 2 illustrates a right side view of the syringe pump.
Figure 3:
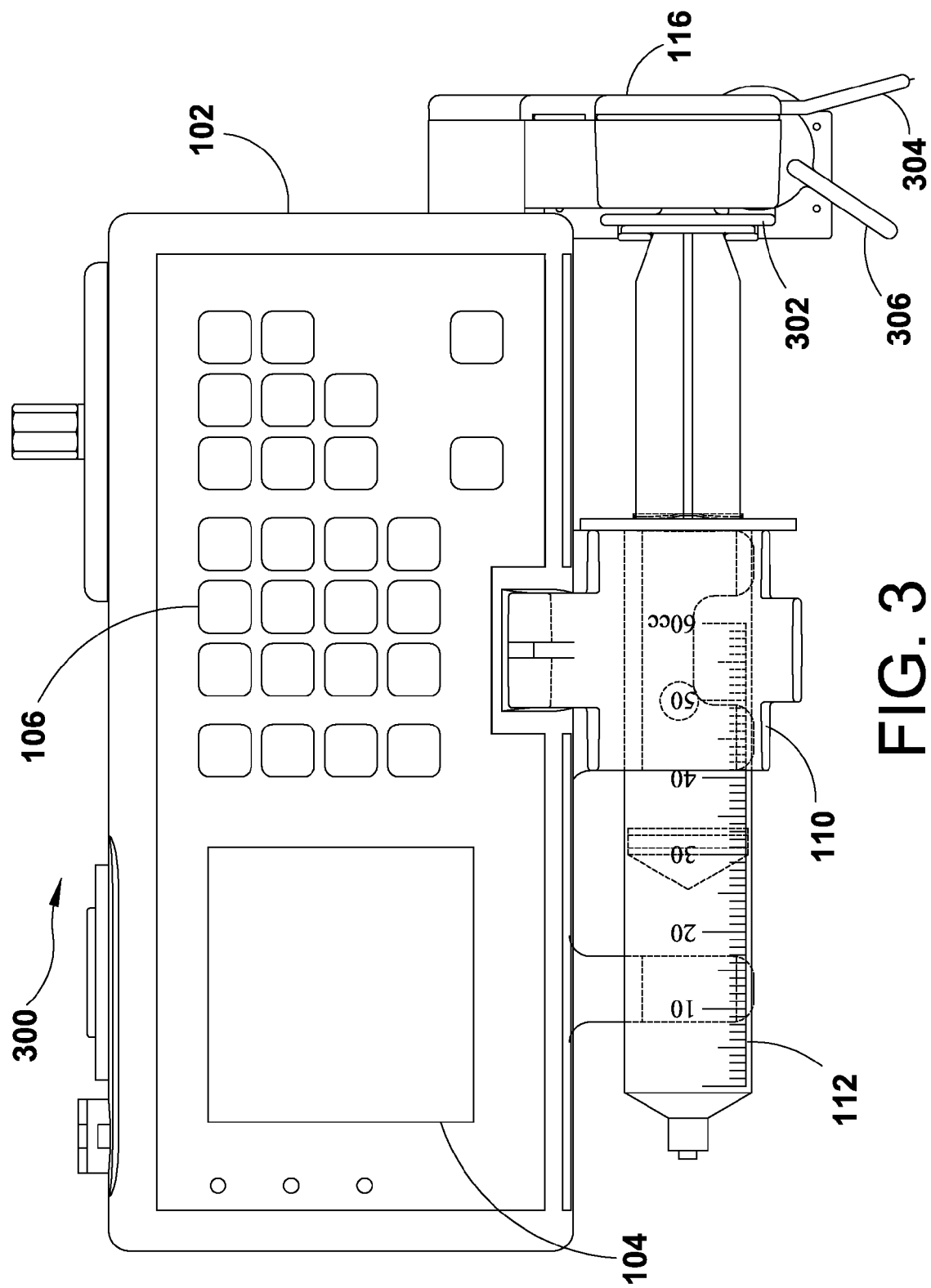
FIG. 3 illustrates a top view of the syringe pump.

FIG. 2 is a right side view 200 of the syringe pump 100. FIG. 3 is a top view 300 of the syringe pump 100. The disc 302 of the syringe plunger 114 is engaged to the plunger holding device 116. The plunger holding device 116 is equipped with a first clutch handle 306 and a second handle 304. The first clutch handle 306 is mobile and the second handle 304 is fixed. When the first clutch handle 306 is pressed against the second handle 304, the plunger holding device 116 is disengaged from the leadscrew.

Figure 4:
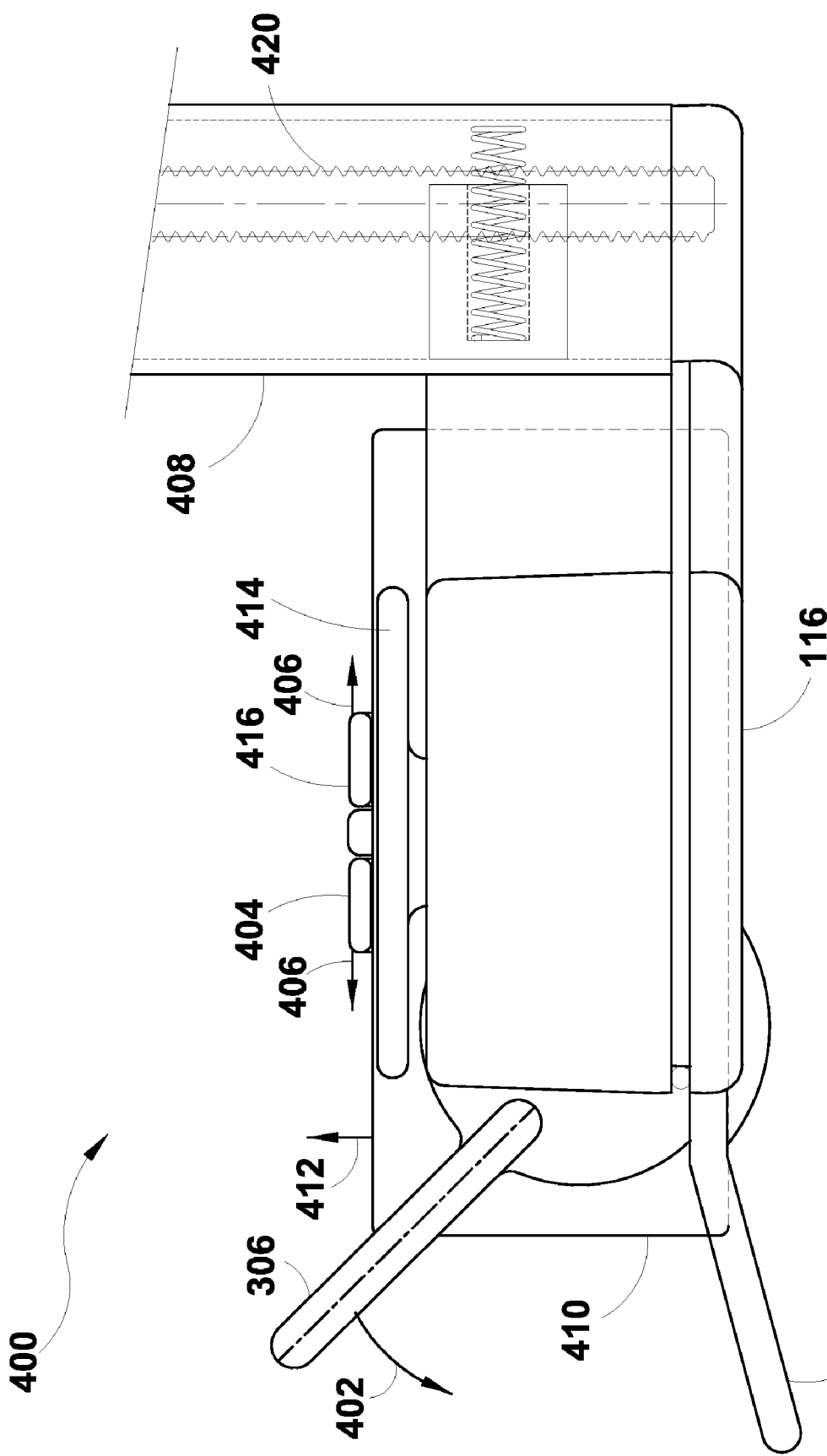
FIG. 4 illustrates a plunger disc holding device of the syringe pump.

FIG. 4 illustrates top view of the plunger holding device 116 attached to the slidable track 408. The plunger holding device 116 has a retainer housing 410, a first clutch handle 306, a second handle 304, a first movable retainer bar 404, a second movable retainer bar 416, and a force sensing plate 414. The first clutch handle 306 is movable and can be moved along a radius when a force 402 is applied. When the first clutch handle 306 moves radially, the retainer housing 410 will move slightly along the y-axis as shown by arrow 412, and the first movable retainer bar 404 and the second movable retainer bar 416 will move away from each other as shown by arrows 406. The first movable retainer bar 404 and second movable retainer bar 416 are preferably two straight bars, parallel to each other. However, other shapes of retainer bars may also be used.

Figure 5:
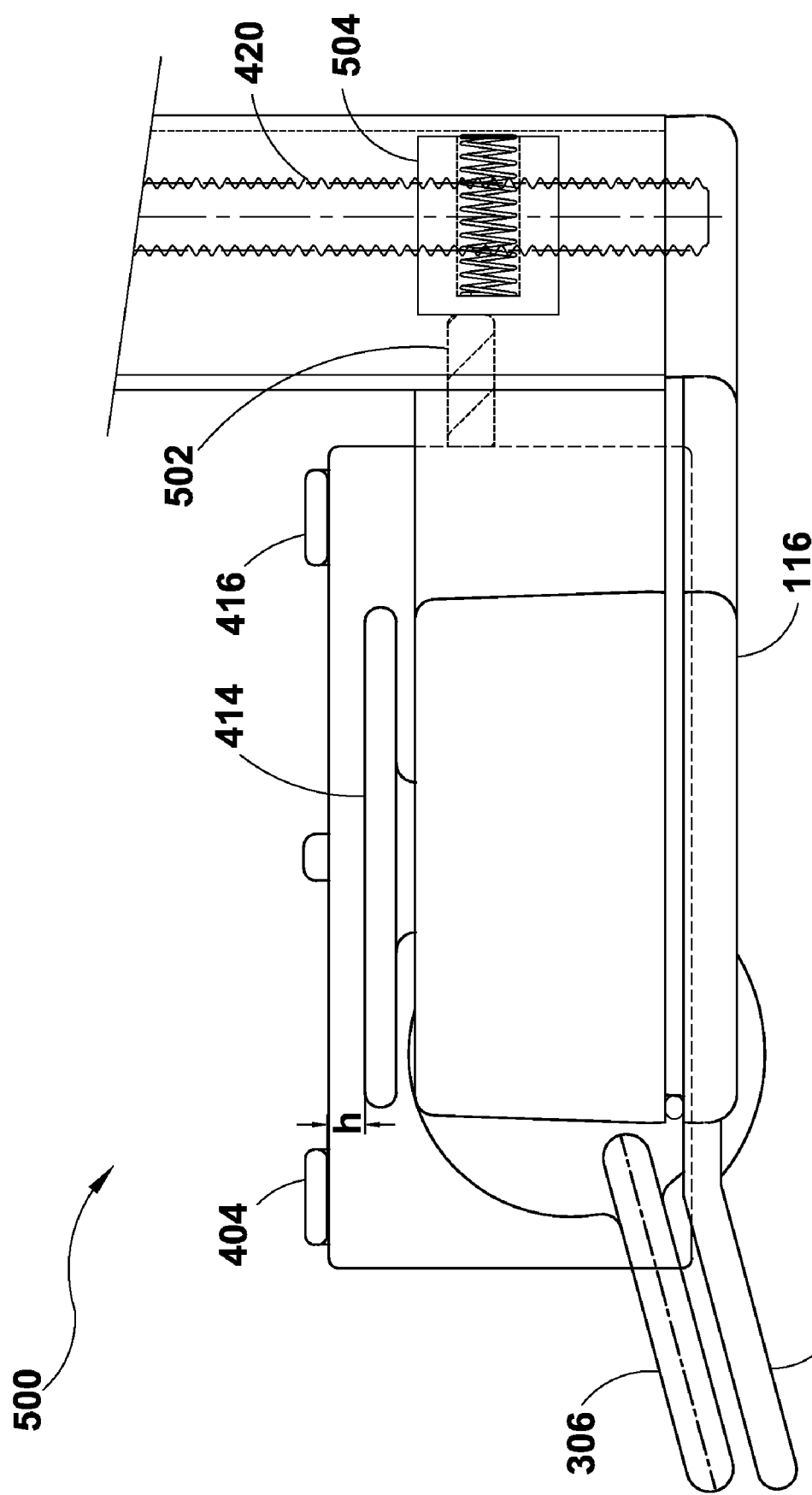
FIG. 5 illustrates the holding device in an actuated position.

As the retainer housing 410 moves along the y-axis and the movable retainer bars 404, 416 move away from each other, a slight gap "h" (shown in FIG. 5) will open between a vertical plan defined by the retainer bars 404, 416 and the vertical surface of the force sensing plate 414. As shown in FIG. 5, as the first clutch handle 306 approaches the second handle 304, a clutch release bar 502 will extend from the plunger holding device 116 into the slidable track 408 to press the clutch pusher 504 to disengage the clutch (not shown) with the leadscrew 420. When the clutch is disengaged, the plunger holding device 116 can move freely along the leadscrew 420. As it is shown in FIG. 5, the first movable retainer bar 404 is separated from the second movable retainer bar 416, thus allowing discs 302 of different diameters to be loaded easily.

Figure 6:
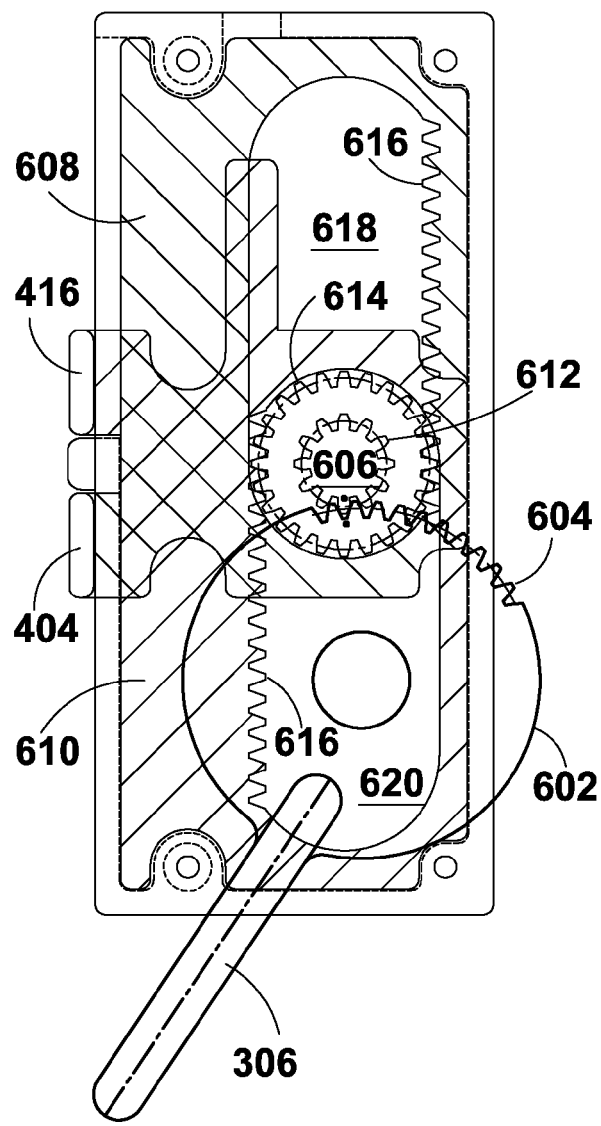
FIG. 6 illustrates an internal mechanism of retainer bars of the plunger disc holding device in a relaxed position.
Figure 7:
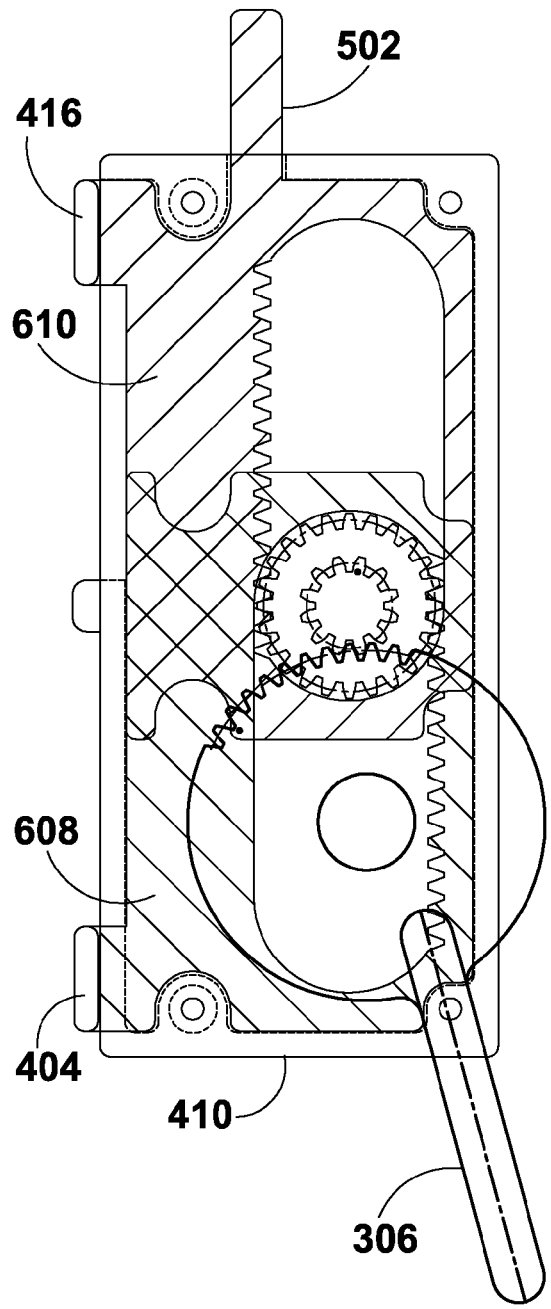
FIG. 7 illustrates the internal mechanism of the retainer bars in the actuated position.

FIG. 6 illustrates internal mechanism of movable retainer bars according to one embodiment of the invention. The first clutch handle 306 is an integral part of a circular disc 602 that has teeth 604 in one part of the circular disc 602. The teeth 604 engage to a small gear 612 of a cluster gear 606. The cluster gear 606 has a small gear 612 on the top and a large gear 614 in the bottom. The large gear 614 is placed in the intersection of two moving plates 608, 610, with internal openings 618, 620, and gear rack 616 on the edge of the internal openings 618, 620. The gear rack 616 of the moving plate 608 is located on the opposite side of the gear rack 616 of the moving plate 610. The first movable retainer bar 404 is an integral part of the moving plate 608, and the second movable retainer bar 41 is an integral part of the moving plate 610. The first clutch handle 306 is attached to a torsion spring 802 (shown in FIG. 8) with a pre-loaded force and the first clutch handle 306 stays in its relaxed position because of the torsion spring 802. When the first clutch handle 306 moves counter-clockwise, the cluster gear 606 rotates clockwise and the large gear 614 engages the gear rack 616 of both moving plates 608, 610. As the large gear 614 rotates clockwise, the moving plate 608 moves from the top position on FIG. 6 to the bottom position on FIG. 7. Similarly, the moving plate 610 moves from the bottom position on FIG. 6 to the top position on FIG. 7. When the moving plates 608, 610 change their positions, the movable retainer bars 404, 416 also change their positions. FIG. 7 illustrates the final position of the moving plates 608, 610 when the first clutch handle 306 reaches its final position. At this position, the clutch release bar 502 is extended outside of the retainer housing 410.

Figure 8:
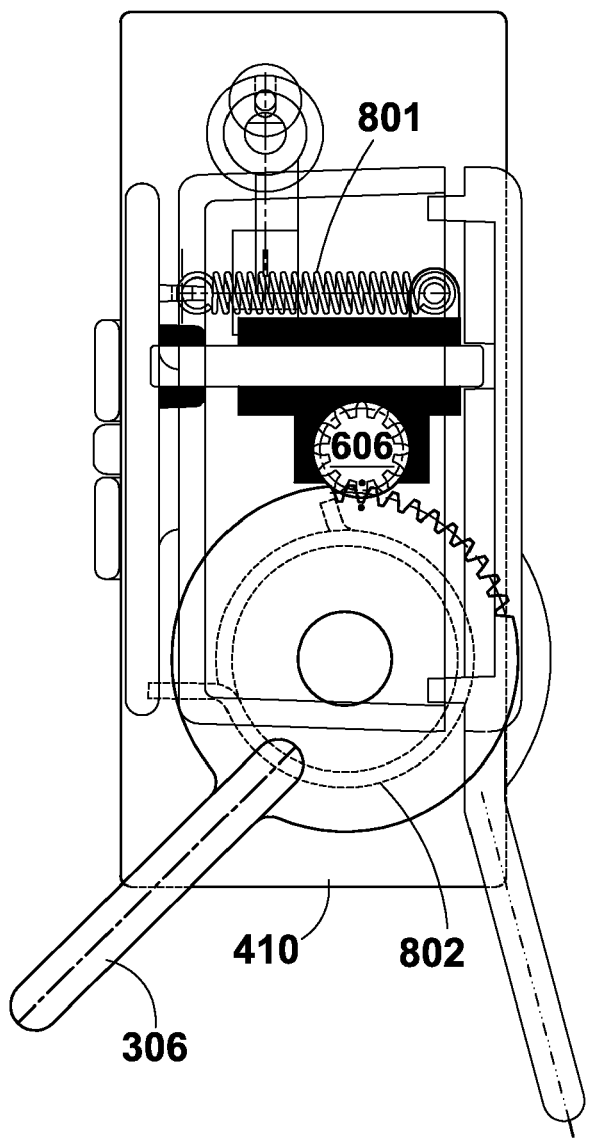
FIG. 8 illustrates a retainer housing of the plunger holding device.
Figure 9:
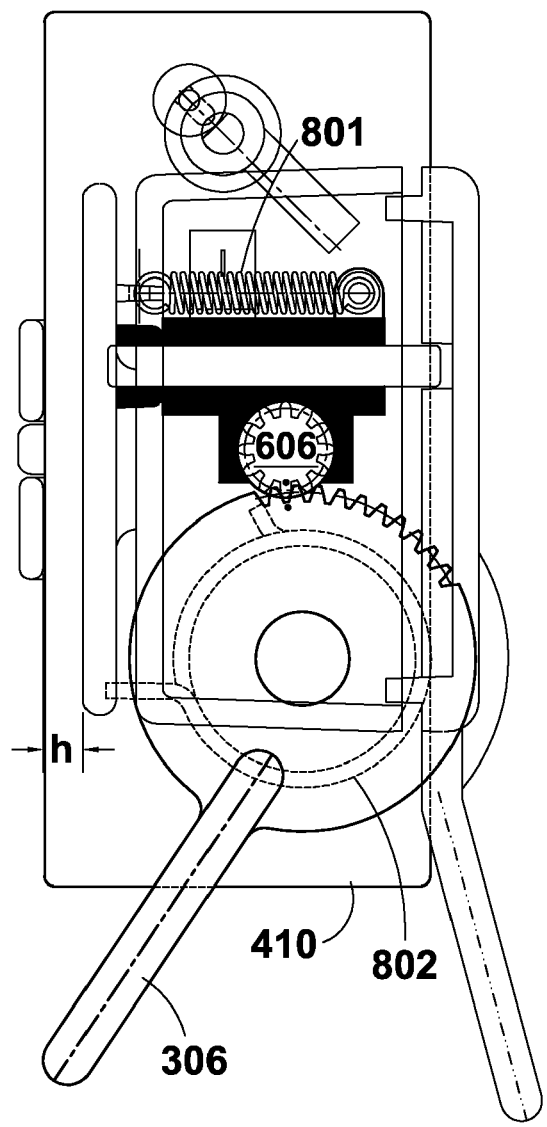
FIG. 9 illustrates the retainer housing of the plunger holding device when the first clutch handle is partially actuated.
Figure 10:
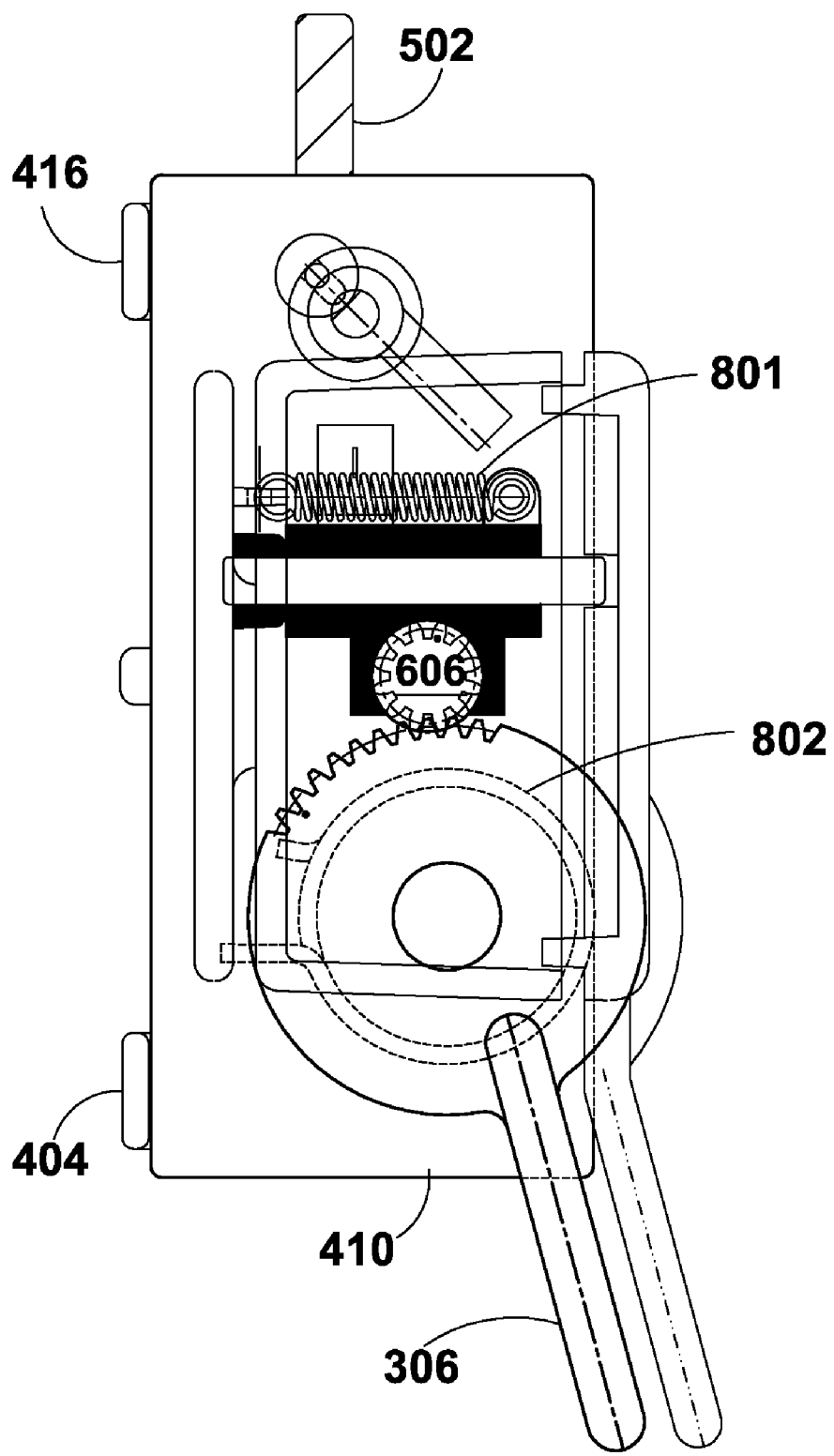
FIG. 10 illustrates the retainer housing of the plunger holding device in the fully actuated position.

FIGS. 8, 9, and 10 illustrate the movement of the retainer housing 410 and retainer bars 404, 416 when the first clutch handle 306 is pressed. FIG. 8 illustrates the retainer housing 410 in the rest condition. FIG. 9 illustrates the first action when the first clutch handle 306 is partially pressed. The cluster gear 606 in the center will not rotate and any rotation on the first clutch handle 306 will translate into sliding movement on the retainer housing 410. The reason for which the cluster gear 606 does not rotate before the sliding of the retainer housing 410 is that it takes more force to rotate the cluster gear 606 to move the retainer bars 404, 416 outward than to slide the retainer housing 410. The reason behind the more force for rotating the cluster gear 606 is that the torsion spring 802 is attached to the first clutch handle 306 and there is an extension spring 801 connecting the back side of sensing plate 414 and the rear side of the retainer housing 410 to pull the retainer housing 410 forward. When the first clutch handle 306 is actuated just a little bit, the extension spring 801 will slide the retainer housing 410 forward. Thus, the retainer housing 410 is moved first until it reaches a stop position, which is defined by the force sensing plate 414 and from where it takes more force to slide the retainer housing 410 than to rotate the cluster gear 606. When the first clutch handle 306 is continued to be actuated and the torsion spring 802 compressed, the first clutch handle 306 will rotate the cluster gear 606 to move the retainer bars 404, 416 outward. FIG. 10 illustrates the first clutch handle 306 in its actuated position with the retainer bars 404, 416 positioned away from each other. This open position facilitates the plunger holding device to be moved to the end of the plunger disc and position the retainer bars in front of the plunger disc. The same principle applies in the reverse operation when the retainer bars 404, 416 are at an outward position. When the first clutch handle 306 is released, the torsion spring 802 inside the first clutch handle 306 expands and forces the first clutch handle 306 to swing back to the relaxed position. The retainer bars 404, 416 first move toward each other. After they reach the inward position (as stopped by the syringe plunger), the retainer bars 404, 416 together with the retainer housing 410 slide toward the force sensing plate 414 to eliminate any gap between the retainer bars 404, 416 and the plunger disc 302. Thus, the plunger disc 302 is firmly held between the retainer bars 404, 416 and the force sensing plate 414 by the preloaded force of the torsion spring 802.

Figure 11:
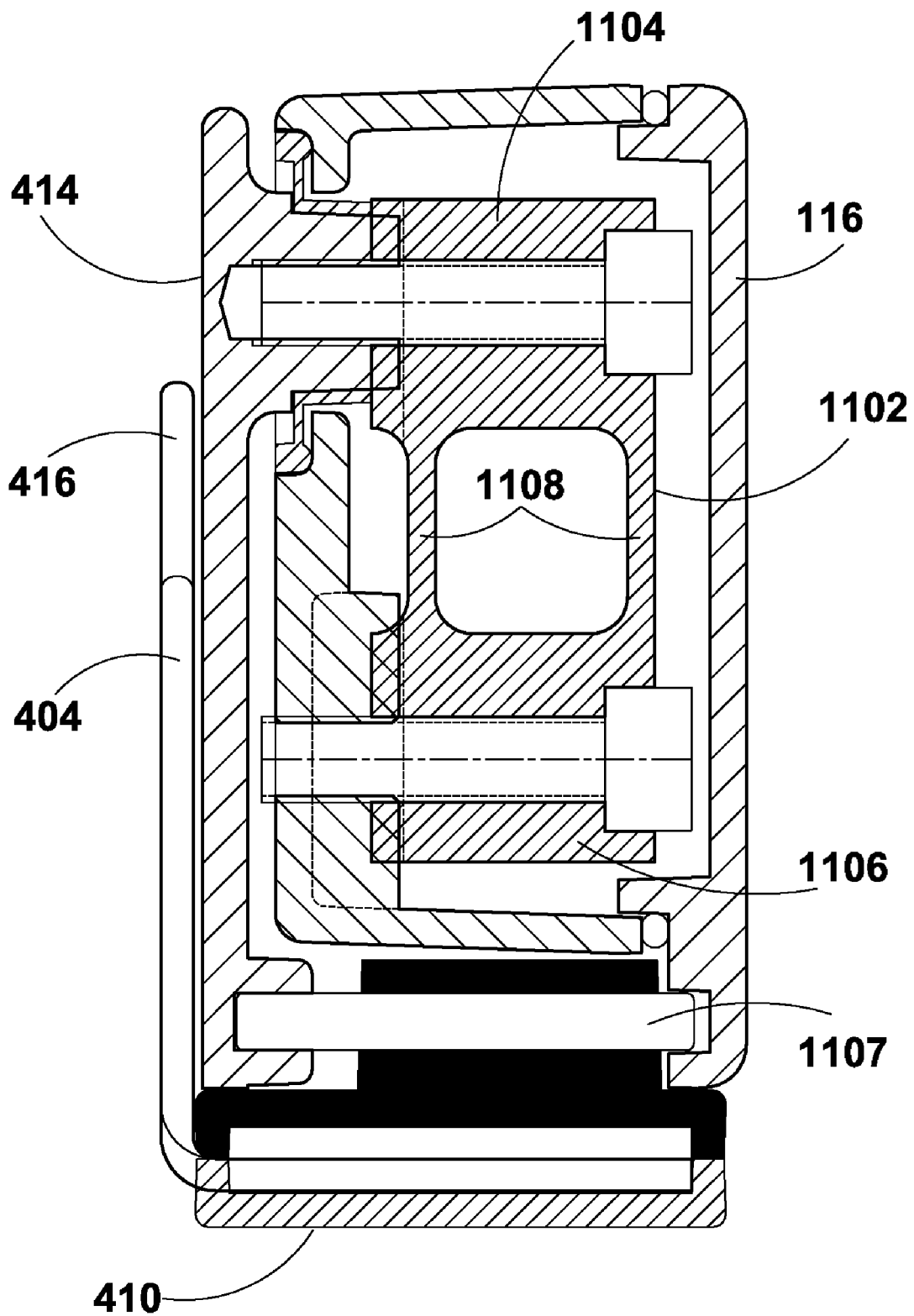
FIG. 11 illustrates a cross section view of the plunger holding device.
Figure 12:
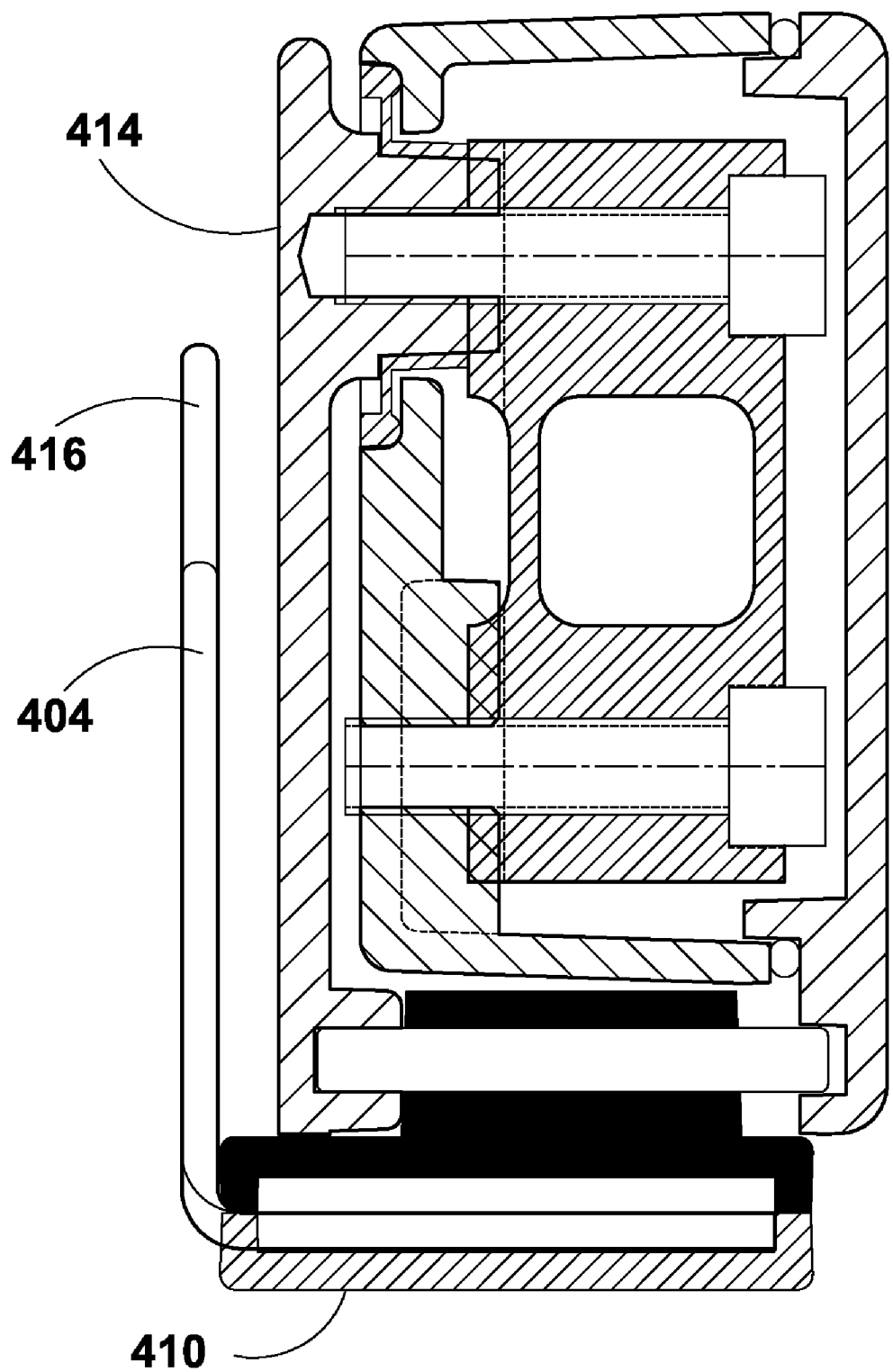
FIG. 12 illustrates a cross section view of the plunger holding device in an actuated position.

FIG. 11 illustrates a cross section view of a plunger holding device 116. The retainer housing 410 is attached to the plunger holding device 116. The force sensing plate 414 is affixed to a force sensor 1102 inside the plunger holding device 116. The force sensor 1102 is a double-beam force transducer that has a squared "O" shape with an upper portion 1104 and a lower portion 1106 connected through two parallel transducer beams 1108. The force sensor 1102 is attached to the plunger holding device 116 through the lower portion 1106 and the force sensing plate 414 is attached to the upper portion 1104. When a force is exerted on the force sensing plate 414, the force sensing plate 414 forces against the sensor 1102, which is attached to a strain gauge and sensing circuit (not shown), and a force measurement can be taken from the sensing circuit. Because the retainer housing 410 is sliding on a dowel pin 1107 that is part of the force sensing plate 414, no force is detectable at the force sensing plate 414 when a plunger disc 302 is held against the force sensing plate 414 by a force from the retainer bars 404, 416. The force sensing plate 414 will detect the pushing force at the plunger disc 302 when the plunger holding device 116, moved by the leadscrew 420, pushes against the plunger disc 302. The fact of the retainer housing 410 being slidable over the dowel pin 1107 prevents introduction of error in sensing and detecting of the pushing force on the plunger disc 302. FIG. 12 is a cross section view of the plunger holding device 116 when the retainer hosing 410 is in an actuated position in which the retainer bars 404, 416 are away from the force sensing plate 414

In operation, a user can place a syringe with fluid on the syringe saddle 108 and secure it with the syringe barrel clamp 110. After the syringe 112 is secured on the syringe pump 102, the user can press, the first clutch handle 306 against the second handle 304, thus disengaging the plunger holding device 116 from the leadscrew 420 inside the slidable track 408. The user can move the plunger holding device 116 closer to the syringe 112 and place the disc 302 of the syringe 112 between two movable retainer bars 404, 416. After the disc 302 is placed between the two movable retainer bars 404, 416, the user can release the first clutch handle 306. After the clutch handle 306 is released, two movable retainer bars 404, 416 will retract, the retainer housing 410 will slide back over the dowel pin 1107, and two movable retainer bars 404, 416 will hold the plunger disc 302 against the force sensing plate 414. Though the plunger disc 302 is held between the movable retainer bars 404, 416 and the force sensing plate 414, no reading is detected by the force sensing plate 414 until the plunger holding device 116 starts to push the plunger disc 302. When the first clutch handle 306 is released, the plunger holding device 116 is engaged to the leadscrew 420. As the syringe pump 102 operates, the plunger holding device 116 moves along the axis of the leadscrew 420, thus pushing the disc 306 and the plunger 114 and the fluid will be delivered through the nozzle 118 of the syringe 112. The fluid delivery rate can be controlled by the syringe pump 102 with the use of the control panel. The pushing force for the syringe plunger can be monitored by the force sensing plate 114 to detect an occlusion condition in the fluid line connected to the syringe nozzle.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Other modifications, variations, and alternatives are also possible. Accordingly, the claims are intended to cover all such equivalents. Dimensions in the drawings here presented are not to scale unless otherwise indicated.

What is claimed is:
1. A syringe pump, comprising:
a housing;
a syringe saddle attached to the housing;
a syringe barrel clamp attached to the housing;
a slidable track connected to the housing;
a plunger holding device attached to the slidable track;
a first movable retainer bar and a second movable retainer bar connected to the plunger holding device, the first movable retainer bar defining a first longitudinal axis and the second movable retainer bar defining a second longitudinal axis, the first longitudinal axis being parallel to the second longitudinal axis; and
an activation mechanism connected to the plunger holding device for moving the first movable retainer bar and the second movable retainer bar away from the plunger holding device and away from each other such that the first longitudinal axis is moved away from the second longitudinal axis while maintaining the first longitudinal axis parallel with the second longitudinal axis,
wherein a disc of a plunger can be held by the first movable retainer bar and the second movable retainer bar and between the first and second movable retainer bars and the plunger holding device.

2. The syringe pump of claim 1, further comprising a leadscrew placed inside the slidable track, the lead screw being capable of sliding the slidable track and moving the plunger holding device along the slidable track.

3. The syringe pump of claim 2, further comprising a release bar connected to the plunger holding device for disengaging the leadscrew from the slidable track when the activation mechanism is actuated.

4. The syringe pump of claim 1, further comprising a sensing plate connected to the plunger holding device, wherein when the first movable retainer bar moves away from the second movable retainer bar, the first movable retainer bar and second movable retainer bar also move away from the sensing plate.

5. The syringe pump of claim 4, further comprising a sensor attached to the sensing plate.

6. The syringe pump of claim 4, further comprising a dowel pin attached to the sensing plate.

7. The syringe pump of claim 6, further comprising a retainer housing connected to the plunger holding device and slidable over the dowel pin, wherein the retainer housing moves away from the sensing plate.

8. The syringe pump of claim 7, further comprising an extension spring connecting the sensing plate to the retainer housing.

9. The syringe pump of claim 5, wherein the sensor is capable of detecting force exerted on the sensing plate.

10. The syringe pump of claim 7, wherein the first movable retainer bar and the second movable retainer bar are connected to the retainer housing and hold the disc of the plunger but exert no influence on a pressure detected by the sensor from pushing the plunger of the syringe.

11. The syringe pump of claim 1, wherein the activation mechanism further comprising a first clutch handle and a second handle, the first clutch handle moving toward the second handle causes the first movable retainer bar and the second movable retainer bar to move away from the plunger holding device.

12. The syringe pump of claim 11, further comprising a torsion spring attached to the first clutch handle.

\* \* \* \* \*